United States Patent [19]
Richelsoph

[11] Patent Number: 5,358,524
[45] Date of Patent: Oct. 25, 1994

[54] ADJUSTABLE LENGTH PROSTHETIC IMPLANT

[75] Inventor: Marc E. Richelsoph, Cordova, Tenn.

[73] Assignee: Wright Medical Technology, Inc., Arlington, Tenn.

[21] Appl. No.: 17,567

[22] Filed: Feb. 16, 1993

[51] Int. Cl.⁵ .............................................. A61F 2/28
[52] U.S. Cl. .................................... 623/16; 623/18; 623/38; 403/109; 403/46
[58] Field of Search .................... 403/26, 43, 46, 118, 403/296, 106, 107, 109; 623/16, 38, 18; 606/63

[56] References Cited

U.S. PATENT DOCUMENTS

| | | | |
|---|---|---|---|
| 1,934,910 | 11/1933 | Buhr | 403/118 X |
| 2,395,332 | 2/1946 | Layman | 403/118 X |
| 2,955,854 | 10/1960 | Musser | 403/107 |
| 3,947,897 | 4/1976 | Owens | 623/16 |
| 4,216,550 | 8/1980 | Thompson | 623/38 X |
| 4,227,518 | 10/1980 | Aginsky | 606/63 |
| 4,502,160 | 3/1985 | Moore et al. | |
| 4,611,944 | 9/1986 | Larson | 403/118 X |
| 4,892,546 | 1/1990 | Kotz et al. | 623/18 |
| 4,988,361 | 1/1991 | Cooper | 623/38 |
| 5,116,335 | 5/1992 | Hannon et al. | 606/62 |

FOREIGN PATENT DOCUMENTS

| | | | |
|---|---|---|---|
| 0212192 | 3/1987 | European Pat. Off. | |
| 2827092 | 1/1980 | Fed. Rep. of Germany | 403/46 |
| 1237192 | 6/1986 | U.S.S.R. | 623/16 |
| 1325228 | 7/1987 | U.S.S.R. | 403/43 |

Primary Examiner—David H. Willse

[57] ABSTRACT

An adjustable length prosthetic implant includes a stem having a threaded portion and an end portion adapted for mounting with a bone. A barrel includes an end portion adapted for mounting with a bone and a sleeve portion extending therefrom and including an elongated chamber defining an axial dimension. The sleeve portion overlies at least a portion of the threaded portion of the stem. A connecting mechanism is mounted on the barrel for interconnecting the barrel and stem and for controlling the axial extension and retraction of the stem from the barrel.

2 Claims, 2 Drawing Sheets

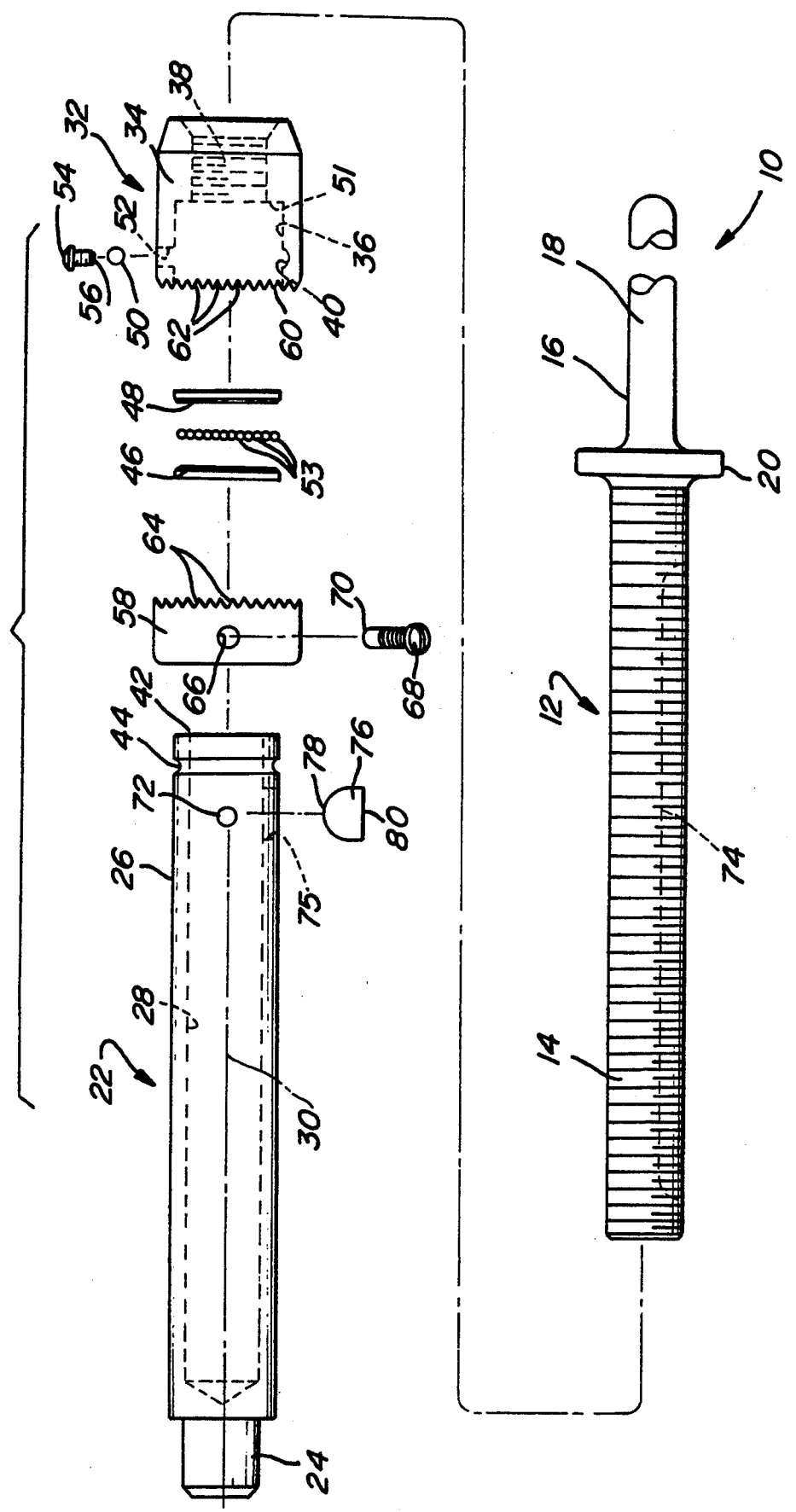

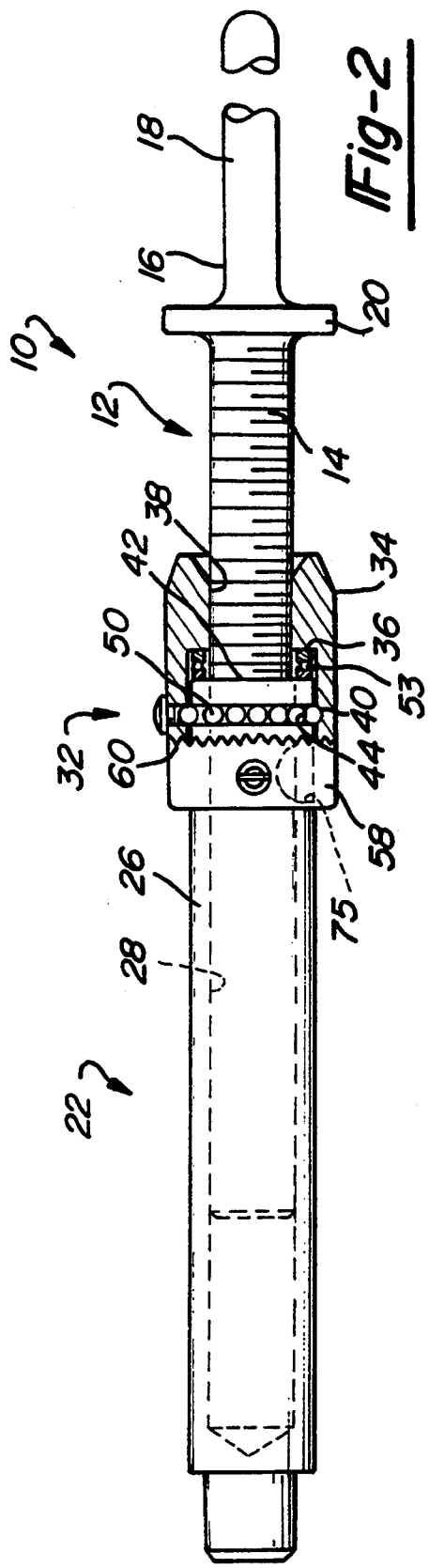
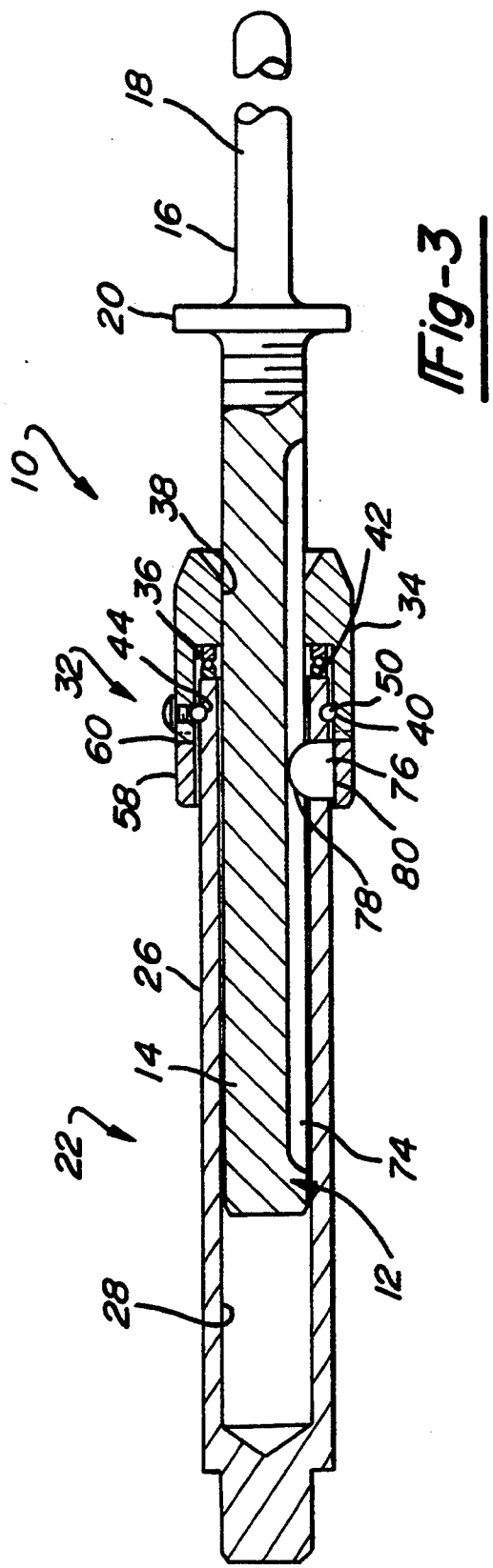

ADJUSTABLE LENGTH PROSTHETIC IMPLANT

TECHNICAL FIELD

The present invention relates to a surgically implantable prosthesis and more particularly is directed to a prosthesis suitable for femoral or humeral components in juvenile patients which provides for adjustment as the patient grows.

BACKGROUND OF THE INVENTION

Many types of skeletal implants and skeletal joint prostheses are available as substitutes for natural skeletal components and joints. Such prostheses are used when the natural skeletal component has been damaged by disease or trauma. However, a problem exists in the case of juvenile patients or other patients where natural growth would otherwise be occurring. As the patient grows, the limb having the prosthesis implanted will not grow at the same rate as the opposing limb unless the prosthesis allows for growth along its length.

The U.S. Pat. 4,892,546 to Kotz et al. issued Jan. 9, 1990 discloses an adjustable prosthesis for a bone joint including a joint component, an elongated rod having a distal end and proximal end, a drive trunion connected to the rod through an angular gear, an elongated inner sleeve and outer sleeve, and means for preventing rotation of the inner sleeve within the outer sleeve. The elongated rod includes a threaded spindle and the inner sleeve includes a threaded spindle nut which cooperates with the threaded spindle to provide extension and retraction adjustment of the rod relative to the inner sleeve. The European patent application EP 86109228, assigned to Waldemar Link GMBH, discloses an endoprosthesis replacing bone middle sections including a tubular spacer with a collar at each end and a solid bone nail extending from one collar. A sliding nail fits in a bore of the tubular spacer and can be locked in any required position by a lock screw.

A joint implant is disclosed in the U.S. Pat. 4,502,160 to Moore et al, issued Mar. 5, 1985, and assigned to the assignee of the present invention. The Moore et al. patent discloses an implant including a stem for bone implantation including a threaded portion for adjusting axially with respect to an overlying sleeve which carries an articulating component of the joint. A pin in the sleeve and an elongated slot in the stem restrain relative rotation but allow axial relative movement as the stem is urged into or out of the sleeve by the rotation of a nut coacting with the threads on the stem while being axially restrained by the sleeve. The nut acts as a ring gear.

Although the Moore et al. patent discloses a very useful embodiment for the prosthetic joint implant, there are several problems that have been encountered with its use. First, the nut interconnecting the stem with the sleeve or barrel is held on the sleeve by two pins which engage an annular slot disposed about the outer surface of the sleeve. This connection fixes the nut axially relative to the sleeve while allowing rotation of the nut, the rotation extending or retracting the stem member. However, the two pins provide a limited two point contact area between the nut and the barrel about which the nut is rotating. There is a torquing force on the pins which results in friction, thereby increasing the torque necessary to rotate the nut. Further, the round pin ends on the flat surface of the groove on the sleeve causes further friction. A second problematic area results from the end of the barrel contacting an inner surface of the nut. Again, this creates a force or friction which must be overcome. Since these parts are generally made out of biocompatable titanium and titanium is susceptible to galling, such metal to metal contact and the resulting friction should be avoided. However, the juxtaposition of the inner surface of the nut and end of the barrel is necessary since there is only a two point contact between the means retaining the nut on the barrel and the barrel itself.

An additional problem is galling of the threads of the stem caused by the threaded engagement and forces with the threaded inner surface of the nut. These strains can result in increased wear of the unit.

The present invention provides an improvement over the implant disclosed in the Moore et al. patent by providing means for reducing and minimizing the relative friction between the nut member and the sleeve as well as increasing fatigue strength of threaded areas of the device thereby decreasing wear of the parts.

SUMMARY OF THE INVENTION

In accordance with the present invention, there is provided a adjustable length prosthetic implant including a stem having a threaded portion and an end portion adapted for mounting with a bone. A barrel includes an end portion adapted for mounting with a bone and a sleeve portion extending therefrom. The barrel includes an elongated chamber defining an axial dimension and overlying at least a portion of the threaded portion of the stem. Connecting means mounted on the barrel interconnects the barrel and stem and controls the axial extension and retraction of the stem from the barrel. Bearing means connects the connecting means to the barrel to prevent relative axial movement therebetween while allowing relative rotation therebetween about the axis and spacing the connecting means from the barrel to minimize relative friction therebetween the relative rotation.

An enhanced bearing surface, such as ball bearings, ceramic disk, other low friction material, or surface treated to enhance anti-galling properties is positioned between the connecting means and end of the barrel.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is an exploded view of a preferred embodiment of the invention;

FIG. 2 is a side view in elevation, partially broken away of the invention; and

FIG. 3 is a cross sectional view of the stem member disposed within and locked from rotation within the barrel of the invention.

DESCRIPTION OF THE PREFERRED EMBODIMENT

An adjustable length prosthetic implant constructed in accordance with the present invention is generally indicated at 10 in the Figures. More specifically, the prosthesis includes a stem generally shown at 12 including a threaded portion 14 and an end portion 16. The end portion is adapted for mounting with a bone. For example, the stem may be in the form of an elongated rod, a taper, or other femoral or humeral component 18. This portion is preferably noncircular in cross section to minimize the possibility of rotation after implantation. The stem 12 includes an intermediate collar 20 which is adapted to overlie a portion of the prepared bone into which the stem 12 is implanted to provide support therefore and to serve to limit growth of bone spurs which occasionally grow from amputated bone in juveniles.

A barrel is generally shown at 22. The barrel 22 includes an end portion 24, shown in FIG. 1, adapted for mounting with a bone. For example, the end portion 24 could be a stud for fitting into a femoral/humeral component or a taper. Alternatively, the end portion 24 could be in the form of an articulating component having condylar portions designed to articulate with the patella and a tibial component for articulation therewith. That is, the present invention can be adapted for insertion between bone parts or ends of bones to function as a prosthetic joint, depending upon the end portion components of the device and particularly of the stem 12 and barrel 22.

The barrel 22 also includes a sleeve portion 26 extending from the end portion 22 and including an elongated chamber 28 along the length thereof defining an axial dimension indicated by hatched line 30 in FIG. 1. The sleeve 26 overlies at least a portion of the threaded portion 14 when the device is assembled, as shown in FIGS. 2 and 3. That is, the threaded portion 14 of the stem 12 is matingly received within the chamber 28 of the barrel 22 for extension therefrom along axis 30.

Connecting means generally indicated at 32 in FIGS. 1 and 2 is mounted on the sleeve portion 26 of the barrel 22 for interconnecting the barrel 22 and stem 12 and controlling the axial extension of the stem 12 from the barrel 22. Bearing means connects the connecting means 32 to the barrel 22 to prevent relative axial movement therebetween while allowing relative rotation therebetween about the axis and spacing the connecting means 32 from the barrel 22 to minimize relative friction therebetween during the relative rotation. The bearing means provides a substantially continuous annular interconnection between the connecting means 32 and sleeve 26 of barrel 22 allowing for rotation of the connecting means 32 about the barrel 22 while maintaining the barrel fixed on the axial dimension 30 relative to the barrel 22. Thus, unlike the two point connection disclosed in the Moore et al. patent, the present invention provides a stable continuous connection about the circumference of the barrel 22 by the inner circumference of the connecting means 32.

More specifically, the connecting means 32 includes a nut member 34 having a passageway 36 extending therethrough, the passageway 36 having an inner surface. The inner surface of the passageway 36 includes a threaded portion 38 for threaded engagement with the threaded portion 14 of the stem 12, as shown in FIG. 2. An annular groove 40 encircles the passageway 36. The barrel 22 includes a second end portion 42 axially opposite the first end portion 24 and having an outer surface. The outer surface includes a second annular groove or recess 44 thereabout. The recesses 40,44 define a pair of opposed races when the nut member 34 is disposed over the second end portion 42 of the barrel 22. The bearing means includes a plurality of roller or preferably ball bearings 50 disposed between the races 40,44, with the pair of opposed races 40,44 entrapping the ball bearings therebetween.

As shown in FIG. 2, the ball bearings 50 space the outer surface of the end portion 42 of the barrel 22 from the inner surface of the nut member 34 while providing a stable interconnection therebetween. Thusly, the ball bearings 50 provide a smoother and stronger mechanism for interconnecting the nut member 34 to the barrel 22. The ball bearings 50 provide for axial retention of the nut member 34 relative to the barrel 22 while allowing rotation of the nut member 34 about the axis 30 relative to the barrel 22. The ball bearings 50 provide a substantially continuous contact area between the nut member 34 and barrel 22 but also a low friction contact area. Hence, there is very little torquing forces between the nut member 34 and barrel 22 but very high stability.

The nut member 34 includes an outer surface and a port 52 extending from the outer surface and through the groove 40 on the inner surface 36 of the nut member 34. The port 52 allows for insertion of the ball bearings 50 into and removal of the ball bearings 50 from the opposed races 46,48 or from directly between grooves 40,42. A closure mechanism in the form of a pin member 54 is seated within port 52 for retaining the ball bearings 50 within the device. The pin member 54 can have an end portion 56 for forming part of the groove 40 when the pin member 54 is inserted into the port 52. Thusly, the pin member 54 acts as a single ball bearing race which is then inserted into the port 52 to complete the race machined into the nut member 34 and to prevent the ball bearings 50 from falling out.

The nut member 32 includes a wall portion 51 extending radially outwardly from the threaded opening 38 and having an inner surface. The assembly 10 includes second bearing means disposed between the second end portion 42 of the barrel 22 and the inner surface of the radial outwardly extending wall portion 51 of the nut member 32 for providing a stable, low friction interface therebetween. As shown in FIG. 1, the bearing means can include a pair of opposed races 46,48 and roller, or preferably ball bearings 53 disposed therebetween. The ball bearings 53 provide a stable low friction interface between the end portion 42 of the barrel 22 and the wall 51 of the nut member 32. Unlike prior art assemblies wherein there is surface to surface contact between the nut member and the barrel resulting in galling, as well as a high friction connection requiring significant force to rotate the nut member to extend the stem, the present invention provides an extremely low friction interface between the barrel 22 and nut member 32, in combination with the first bearing means connection.

The second bearing means can alternatively take the form of a disk member (not shown) disposed between the end portion 42 and wall 51 of the nut member. Such a disk member can be made from a self-lubricating material, such as TEFLON ® or the like. Alternatively, the disk member can be made from ceramic material. Alternatively, the end portion 42 of the barrel 22 and the wall 51 can be surface treated to enhance anti-galling properties.

The prosthesis 10 includes a rotation locking mechanism for locking the nut member 34 from rotating relative to the barrel 22. More specifically, the nut member 34 includes an end portion 60 axially medial relative to the barrel 22 when it is mounted thereon. The end portion 60 includes a plurality of recesses 62 about the circumference thereof. The recesses can be in the form of gear teeth or the like. The locking mechanism includes a ring member 58 axially moveable over the barrel 22. The ring member 58 includes a plurality of projections 64 which can also be in the form of gear teeth for mating engagement with the recesses 62 in the end portion 60 of the nut member 34.

A mechanism for fixing the locking ring 58 relative to the barrel 22 includes a threaded opening 66 in the locking ring 58 and a locking screw 68 for threaded engagement with the opening 66 and a chuck keyhole 72 which extends through the barrel 22. The screw member 68 fixes the ring member 58 from movement relative to the barrel 22 while the ring member 58 is in mating engagement with the nut member 34, as shown in FIG. 2, to reversibly lock the nut member 34 from rotation relative to the barrel member 22.

An antirotation mechanism prevents relative rotation between the stem 12 and barrel 22. More specifically, the barrel 22 includes an opening 75 extending therethrough. The antirotation mechanism includes a groove 74 extending along a length of the threaded portion 14 of the stem 12 and a key member 76 extending through the opening 75 and seated within the groove 74. The key member 76 includes a polished semi-circular surface 78. The key 76 is self-aligning because it is a highly polished semi-circular disk which is matched to the inside dimensions of the groove 74. The disk 76 is inserted through the opening 75 in the barrel 22, and when fully inserted, engages the groove 74. This provides a single contact point at the disk/groove interface regardless of whether the disk flat face 80 is perfectly parallel to the outside surface of the barrel 22.

In the preferred embodiment of the present invention, all parts including the threads will be treated by ion bombardment, chemicals, or other means to increase fatigue strength and anti-galling properties. For example, ion nitriding and ion implantation are alternative methods which can be utilized. These methods can be made in accordance with reports by Hulett et al., "Ion Nitriding and Ion Implantation: a Comparison", *Metal Products*, August 1985, and Rieu et al., "Ion Implantation Effects on Friction and Wear of Joint Prosthesis Materials", *Bio Materials* 1991, Vol. 12, March. Alternative methods known in the art can also be used.

In use, the prothesis is surgically mounted on the patient's bone providing for the needed joint or other connection. The ring member 58 is slidably disposed on the end portion 26 of the barrel 22 allowing for rotation of the nut member 34. The nut member 34 is rotated on the barrel 22 to allow for the appropriate needed extension of the threaded portion 44 from the chamber 28 of the barrel 22. Since the key member 76 prevents rotation of the stem 22 by mating engagement with groove 74, rotation of the nut member 58 extends or retracts the stem 12 by the threaded engagement between the threaded portion 38 of the nut member 34 and the threaded portion 14 of the stem 12. The ball bearings 50 maintain the nut member 58 at a single axial position relative to the barrel 22. The ball bearings 50 provide a stable interconnection between the nut member 34 and barrel 22 while also providing an extremely low frictional connection.

Once the appropriate adjustment is made, the locking ring 58 is moved axially along the sleeve portion 26 so that the projections 64 of the locking ring 58 mate with recesses 62 in the nut member 34. The locking screw 68 is inserted through the locking ring opening 66 and into port 72 thereby preventing rotation of the locking ring 64. This mechanism also prevents rotation of the nut member 34 and thereby prevents any extension or retraction of the stem 12.

If extension of the stem 12 is required due to growth of the limb, the locking screw 68 is released from opening 72 thereby allowing for rotation of the nut member 34 to extend the stem 12.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims, the invention may be practiced otherwise than as specifically described.

What is claimed is:

1. An adjustable length prosthetic implant comprising:
    a stem including a threaded portion and an end portion adapted for mounting with a bone;
    a barrel including a first end portion adapted for mounting with a bone and a sleeve portion extending therefrom and including an elongated chamber defining an axial dimension and overlying at least a portion of said threaded portion; said barrel including a second end portion axially opposite said first end portion and having an outer surface, said outer surface including an annular groove thereabout;
    connecting means mounted on said barrel for interconnecting said barrel and stem and controlling the axial extension and retraction of said stem from said barrel; said connecting means including a nut member having a passageway extending therethrough having an inner surface, said inner surface including a threaded portion for threaded engagement with said threaded portion of said stem, said inner surface further including an annular groove encircling said passageway;
    bearing means connecting said connecting means to said barrel to prevent relative axial movement therebetween while allowing relative rotation therebetween about said axis and spacing said connecting means from said barrel to minimize relative friction therebetween during said relative rotation, said bearing means including a plurality of roller bearings disposed between said grooves as said grooves define a pair of opposed races entrapping said roller bearings therebetween, said roller bearings spacing said outer surface of said barrel from said inner surface of said nut member while providing a stable interconnection therebetween;
    said nut member including an outer surface and a port extending from said outer surface through said groove in said inner surface allowing for insertion of said roller bearings into and removal of said roller bearings from said opposed races;
    said connecting means including closure means for sealing closed said port, said closure means including a pin member including an end portion for forming part of said groove when said pin member is inserted in said port; and
    rotation locking means for locking said nut member from rotating relative to said barrel;
    said nut member including an end portion axially medial relative to said barrel and including recesses therein, said locking means including a ring member axially movable over said barrel and including projection for mating engagement with said recesses of said nut member, said locking means including fixing means for fixing said ring member from movement relative to said barrel while in mating engagement with said nut member to reversibly lock said nut member from rotation relative thereto.

2. An adjustable length prosthetic implant comprising:
- a stem including a threaded portion add an end portion adapted for mounting with a bone;
- a barrel including a first end portion adapted for mounting with a bone and a sleeve portion extending therefrom and including an elongated chamber defining an axial dimension and overlying at least a portion of said threaded portion; said barrel including a second end portion axially opposite said first end portion and having an outer surface, said outer surface including an annular groove thereabout;
- connecting means mounted on said barrel for interconnecting said barrel and stem and controlling the axial extension and retraction of said stem from said barrel; said connecting means including a nut member having a passageway extending therethrough having an inner surface, said inner surface including a threaded portion for threaded engagement with said threaded portion of said stem, said inner surface further including an annular groove encircling said passageway;
- bearing means connecting said connecting means to said barrel to prevent relative axial movement therebetween while allowing relative rotation therebetween about said axis and spacing said connecting means from said barrel to minimize relative friction therebetween during said relative rotation, said hearing means including a plurality of roller bearings disposed between said grooves as said grooves define a pair of opposed races entrapping said roller bearings therebetween, said roller bearings spacing said outer surface of said barrel from said inner surface of said nut member while providing a stable interconnection therebetween;
- said nut member including an outer surface and a port extending from said outer surface through said groove in said inner surface allowing for insertion of said roller bearings into and removal of said roller hearings from said opposed races;
- said connecting means including closure means for sealing closed said port, said closure means including a pin member including an end portion for forming part of said groove when said pin member is inserted in said port;
- rotation locking means for locking said nut member from rotating relative to said barrel; and
- anti-rotation means for preventing relative rotation between said stem and said barrel;
- said barrel including an opening extending therethrough, said anti-rotation means including a groove extending along a length of said threaded portion of said stem and a key member extending through said opening in said barrel and seated within said groove, said key member including a polished semi-circular surface for providing a single contact point within said groove.

* * * * *